(12) United States Patent
Chiou et al.

(10) Patent No.: US 9,023,341 B2
(45) Date of Patent: May 5, 2015

(54) AMPHIPHILIC CHITOSAN NANOGEL AS AN INJECTABLE DELIVERY SYSTEM FOR STEM CELL THERAPY

(71) Applicant: Taipei Veterans General Hospital, Taipei (TW)

(72) Inventors: Shih-Hwa Chiou, Taipei (TW); Dean-Mo Liu, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 0 days.

(21) Appl. No.: 13/770,418

(22) Filed: Feb. 19, 2013

(65) Prior Publication Data

US 2013/0230495 A1     Sep. 5, 2013

Related U.S. Application Data

(60) Provisional application No. 61/600,187, filed on Feb. 17, 2012.

(51) Int. Cl.
| | |
|---|---|
| *C12N 5/00* | (2006.01) |
| *C12N 5/02* | (2006.01) |
| *A61K 47/36* | (2006.01) |
| *A61L 27/20* | (2006.01) |
| *A61L 27/38* | (2006.01) |
| *A61L 27/50* | (2006.01) |
| *A61L 27/52* | (2006.01) |

(52) U.S. Cl.
CPC ............. *A61K 47/36* (2013.01); *A61L 27/20* (2013.01); *A61L 27/3834* (2013.01); *A61L 27/50* (2013.01); *A61L 27/52* (2013.01); *A61L 2400/12* (2013.01)

(58) Field of Classification Search
None
See application file for complete search history.

(56) References Cited

U.S. PATENT DOCUMENTS

| | | | | |
|---|---|---|---|---|
| 4,659,700 | A * | 4/1987 | Jackson | 514/55 |
| 6,344,488 | B1 * | 2/2002 | Chenite et al. | 514/777 |
| 2007/0128722 | A1 * | 6/2007 | Lin et al. | 435/366 |
| 2010/0098731 | A1 * | 4/2010 | Chen et al. | 424/400 |

OTHER PUBLICATIONS

Liu et al., Langmuir, 22:9740-9745 (2006).*
Tsai et al., NEJM, 343(2):86-93 (2000).*
Chen et al., J. Contr. Rel. 96:285-300 (2004).*
Chenite et al., Biomater., 21:2155-2161 (2000).*
Liu et al., Acta Biomater., 6:1423-1429 (2010).*
Liu et al., Macromol., 41:6511-6516 (2008).*
Ruel-Gariepy et al., Int. J. Pharma., 203:89-98 (2000).*
Mi et al., Biomater., 23:181-191 (2002).*
Mwale et al., Tis. Eng., 11(1/2):130-140 (2005).*
Muzzarelli et al., Carb. Poly., 77:1-9 (2009).*
Roldo et al., Stud. Mechanobiol. Tissue Eng. Biomater., 8: 351-376 (2011).*

* cited by examiner

*Primary Examiner* — Blaine Lankford
*Assistant Examiner* — Thomas J Visone
(74) *Attorney, Agent, or Firm* — Wolf, Greenfield & Sacks, P.C.

(57) ABSTRACT

The present invention relates to a novel injectable delivery system for stem cell therapy, which comprises a thermosensitive amphiphlic chitosan nanogel. Therefore, the invention provides a method for repairing a tissue damage of a subject using the amphiphlic chitosan nanogel served as a carrier for delivering the stem cells to the damaged tissue. This invention also provides a method for sustaining the growth of stem cells using the amphiphlic chitosan nanogel served as a niche or scaffold.

7 Claims, 7 Drawing Sheets

AMPHIPHILIC CHITOSAN NANOGEL AS AN INJECTABLE DELIVERY SYSTEM FOR STEM CELL THERAPY

RELATED APPLICATIONS

This application claims priority under 35 U.S.C. §119 to U.S. provisional application 61/600,187, filed Feb. 17, 2012, the entire content of which is herein incorporated by reference in its entirety.

FIELD OF THE INVENTION

The present invention relates to a method of treating tissue damages by use of hydrogel containing stem cells. In particular, the present invention is directed to the amphiphilic thermo-sensitive nanogel in combination with stem cells for repairing tissue damages of a subject in need thereof. The present invention also relates to use of the amphiphilic nanogel as a niche or scaffold for sustaining the growth of stem cells.

BACKGROUND OF THE INVENTION

Stem cell therapy is now being used to treat a plethora of diseases including leukemia, spinal cord injuries, heart diseases, Parkinson's, Alzheimer's, diabetes and arthritis. Since stem cells are capable of self-renewal and differentiation into a variety of mature cell lineages, transplantation of such cells can be utilized as a clinical tool for reconstituting a target tissue, thereby restoring physiologic and anatomic functionality.

In recent years, thermosensitive injectable hydrogels have attracted a great deal of interest in medical applications since they have a great advantage over conventional implantation surgery as they minimize the invasiveness of the implant procedures. Other advantages include easy handling by clinic personnel, reduced pain, less complications, reduced healing period, minimal scarring, reduced surgery time, and the ability to conform to irregular defects.

Among a number of injectable hydrogel candidates, chitosan (CS), a polysaccharide consisting of β-(1,4)-linked glucosamine units, was widely experimented as a biomaterial. It is known that CS is extracted from fungal cell walls and exoskeletons of arthropods such as crabs, shrimp and krill. It holds several characteristics desirable for biomedical applications, such as; biocompatibility, biodegradation, bioadhesivity, anti-bacterial effects and no toxicity. Given the mentioned properties, CS is an ideal material to be used in biomedical applications where the material will be in contact with the patient for prolonged periods. CS and its derivatives have been widely investigated for applications such as; controlled drug and protein release, non-viral gene delivery and tissue engineering. Many studies elaborated its biocompatibility, solubility, pH sensitivity and thermo-sensitivity by grafting different subgroups to the CS backbone, this in order to impart desired biofunctionality to the resulting hydrogel. To achieve chitosan solutions with thermo-induced gelling, CS is typically mixed with polyol salts such as; disodium-, ammonium hydrogen-, glycerol-, sorbitol-, fructose- or glucose-phosphate salts. These salts form ideal agents for transforming purely pH-dependent chitosan solutions into temperature-controlled pH-dependent chitosan solutions. Such solutions are typically liquids at low temperatures, but form gels at elevated temperatures. This makes them suitable as injectable in vivo gelling systems. After injection, due to the elevated temperature of the host, a gel is formed through temperature induced formation of a connective network, in which co-injected therapeutics are embedded, allowing for subsequent pre-designed medical function.

BRIEF SUMMARY OF THE INVENTION

In the present invention, it is unexpected found that an injectable nanogel made from amphiphilic chitosan that is in a liquid form at a room temperature or below (e.g., about 4~20° C.) but can be gelated at about 30~40° C. to the contrary to conventional biomaterials, can be used for loading and culturing stem cells and then delivering the cultured cells to the site to be implanted for repairing a tissue damage. Accordingly, the invention provides a new approach for stem cell-based therapy using a thermo-gelling injectable nanogel.

In one aspect, the invention provides a method for repairing a tissue damage in a subject comprising injecting an injectable stem cell-based implant to the site of the tissue damage of the subject; wherein the injectable stem cell-based implant is prepared by adding the stem cells of the tissue to a solution of an amphiphilically modified carboxymethyl-hexanoyl chitosan, stabilized by a structural stabilizer; whereby an injectable stem cell-based implant in the form of a solution for injection is obtained, and can be gelated after the injection where the temperature rises to 30~40° C.

In one embodiment of the invention, the amphiphilically modified carboxymethyl-hexanoyl chitosan has s structure of formula (I):

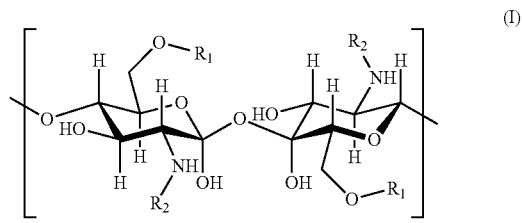

wherein $R_1$ is $CH_2COOH$ or H; and $R_2$ is $CO(CH_2)_4CH_3$, $CH_2COOH$, or $COCH_3$ or H.

In one embodiment of the invention, the solution is prepared by stirring amphiphilically modified carboxymethyl-hexanoyl chitosan with a solvent, which is selected from the group consisting of the group consisting of dimethyl sulfoxide (DMSO), ethanol, glycerol and a combination thereof. In one particular example, the solvent is glycerol. According to the invention, the concentration of the amphiphilically modified carboxymethyl-hexanoyl chitosan is 0.1-10% (w/v).

In one embodiment of the invention, the basic structural stabilizer is selected from the group consisting of genipin, β-glycerol phosphate disodium hydrate, $NaHCO_3$, and a combination thereof. In one particular example, the basic structural stabilizer is β-glycerol phosphate disodium hydrate. According to the invention, the concentration of the basic structural stabilizer to be added is 0.1-10% (w/v).

In another aspect, this invention provides a method of preparing an injectable stem cell-based implant comprising the steps of:

(a) stirring an amphiphilically modified carboxymethyl-hexanoyl chitosan with a solvent to obtain a pre-nanogel solution at a room temperature or below; and (b) adding stem cells and a basic structural stabilizer to the pre-nanogel solution as obtained in step (a) and stirring it thoroughly at a room temperature or below to obtain an injectable stem cell-based implant.

In one embodiment, the temperature at which the solution is kept in the step (a) or (b) is 4~20° C.

According to the invention, the injectable stem cell-based implant as obtained in step (b) may be further cultured for cell growth. In one example of the invention, the injective stem cell-based implant is further cultured at 30~40° C. for gelation and cell growth.

In one embodiment of the present invention, the injectable stem cell-based implant may be topped with a layer of a culture medium for cell proliferation.

In yet another aspect, the present invention also provides an injectable stem cell-based implant, which is prepared by the method according to the invention.

Further provided is a method of repairing a corneal injury in a subject. The method comprises injecting an injectable corneal stem cell-based implant to the injured site of the cornea, wherein the injectable corneal stem cell-based implant is prepared by the method comprising the steps of:
(a) stirring 0.1-10% (w/v) of an amphiphilically modified carboxymethyl-hexanoyl chitosan with a solvent to obtain a pre-nanogel solution at 4~20° C.; and
(b) adding corneal stem cells and 0.1-10% (w/v) of a basic structural stabilizer to the pre-nanogel solution as obtained in step (a) and stirring it thoroughly at 4~20° C. to obtain an injectable corneal stem cell-based implant.

In one example, the method of repairing a corneal injury further comprises applying a cover over the injured site after the injection of the corneal stem cell-based implant.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
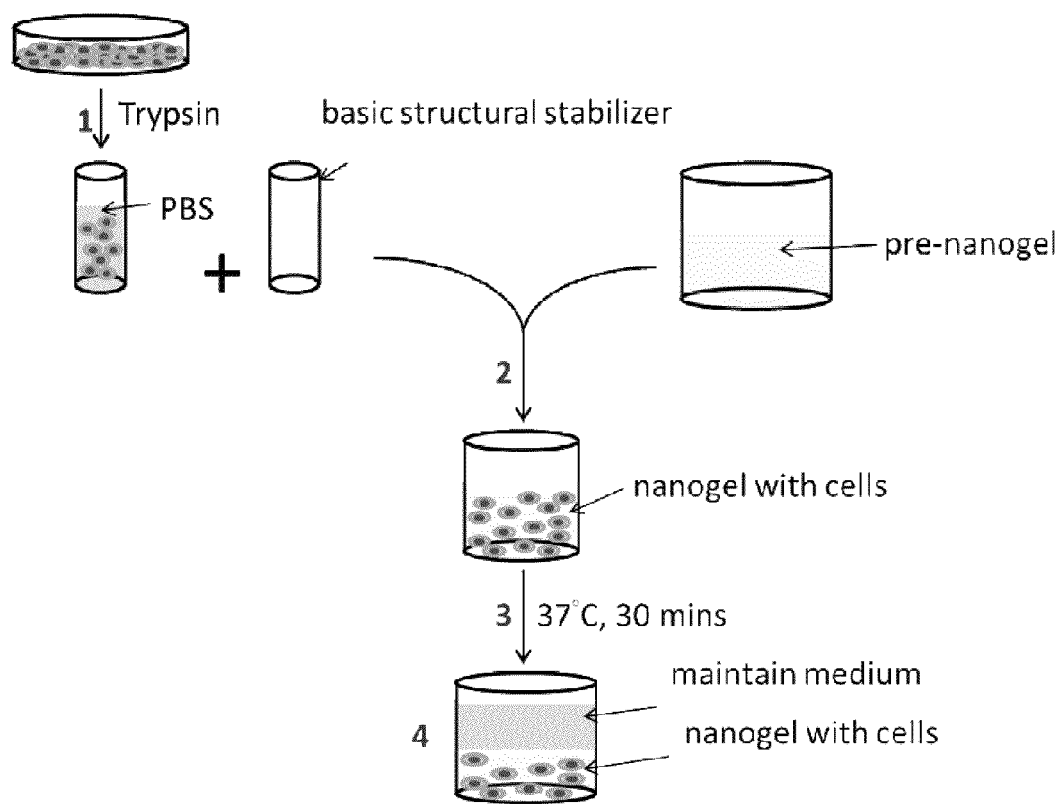
FIG. 1 is a flow chart showing the process for preparing the injectable nanogel for culturing stem cells in vitro.

Unless otherwise defined, all technical and scientific terms used herein have the same meaning as commonly understood by one of ordinary skill in the art to which this invention pertains. In the case of conflict, the present document, including definitions will control.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "subject" refer to a human or a mammal, such as a patient, a companion animal (e.g., dog, cat, and the like), a farm animal (e.g., cow, sheep, pig, horse, and the like) or a laboratory animal (e.g., rat, mouse, guinea pig, and the like).

As used herein, the term "room temperature" refers to common indoor temperatures, usually about 20° C.

According to the present invention, a method for repairing tissue damage in a subject comprises injecting an injectable stem cell-based implant to the site of the tissue damage of the subject. The injectable stem cell-based implant is prepared by adding the stem cells of the tissue to a solution comprising an amphiphilically modified carboxymethyl-hexanoyl chitosan, stabilized by a basic structural stabilizer; whereby an injectable stem cell-based implant in the form of a solution for injection is obtained, and can be gelated after the injection where the temperature rises to 30~40° C.

In one embodiment of the invention, the amphiphilically modified carboxymethyl-hexanoyl chitosan (CHC) has a structure of formula (I):

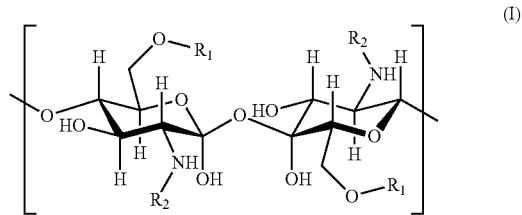

wherein R1 is $CH_2COOH$ or H; and R2 is $CO(CH_2)_4CH_3$, $CH_2COOH$, or $COCH_3$ or H, which is stabilized by a basic structural stabilizer.

The preparation of amphiphilically modified carboxymethyl-hexanoyl chitosan (CHC) has been disclosed in U.S. application Ser. No. 13/079,439, filed on Apr. 4, 2011, which is hereby incorporated by reference entirely. In brief, the amphiphilically modified carboxymethyl-hexanoyl chitosan can be successfully synthesized through modification of native chitosan by hydrophilic carboxymethyl substitution to increase the flexibility of chitosan molecular chain in water and hydrophobic substitution with hexanoyl groups to increase the amphiphilic character. The CHC macromolecules have demonstrated self-assembling capability into nanocapsules about 200 nm in size in aqueous environment, where the capsules have good drug loading properties. In addition, the CHC macromolecules show good water retention capability after swelling in aqueous solution. It is expected that the CHC macromolecule and nanocapsules made therefrom, can possess environmentally-induced gelation under a well-defined chemical environment.

In the present invention, the CHC nanocapsules are used to develop a novel injectable stem cell-based implant for medical applications, such as stem cell-based therapy. In one example of the invention, the injectable stem cell-based implant was obtained by culturing stem cells in a solution of CHC with a small amount of glycerol, which was stabilized by sodium β-glycerophosphate (β-GP) to neutralize the positive charge of the CHC and facilitate a sol-to-gel transition upon a temperature increase. The amphiphilically modified chitosan (CHC) self-assembled into nanocapsules in aqueous environment. At acidic to neutral pH the nanocapsules carried positive charges on their shell, derived from the protonation of amino groups. The CHC solution was virtually a viscous liquid at low temperature, such as 4~20° C., preferably 4~10° C., exhibiting flow under its own weight. The solution of CHC formed a gel when the temperature rose to 30~40° C., such as 37° C. Therefore, the CHC nanogel as formed acted as a scaffold to cultivate stem cells so as to maintain the stemness property of the stem cells, which was evidenced by the cell viability and quantitative PCR assays as shown in the examples. It was found that the rats treated by the implant prepared by the CHC nanogels containing stems cells had significantly improved healing rate of the corneal injury. Therefore, the injectable stem cell-based implant is proved to provide a significantly improved efficacy in repairing tissue damages.

Accordingly, the invention provides a method of preparing an injectable stem cell-based implant, comprises the steps of:
(a) stirring a solution comprising 0.1-10% (w/v) of an amphiphilically modified carboxymethyl-hexanoyl chitosan to obtain a pre-nanogel solution at a room temperature or below; and
(b) adding stem cells and 0.1-10% (w/v) of the basic structural stabilizer to the pre-nanogel solution as obtained in the step (a), and stirring thoroughly at a room temperature or below to obtain an injective stem cell-based implant.

In the invention, the basic structural stabilizer includes, but is not limited to, genipin, β-glycerol phosphate disodium hydrate, NaHCO3 and a combination thereof. In one sample of the invention, the basic structural stabilizer is β-glycerol phosphate disodium hydrate.

In the invention. the solvent includes but is not limited to dimethyl sulfoxide (DMSO), ethanol, glycerol and a combination thereof. Therefore, the solvent is selected from the group consisting of dimethyl sulfoxide (DMSO), ethanol, glycerol and a combination thereof. In one example of the invention, the solvent is glycerol.

In one embodiment of the present invention, the injectable stem cell-based implant may be further topped by a layer of culture medium for cell proliferation.

The present invention also provides an injectable stem cell-based implant as prepared by the methods according to the invention.

In one particular example of the invention, a method of repairing a corneal injury comprises injecting a corneal stem cell-based implant to the injured site of the cornea, wherein the corneal stem cell-based implant is prepared by the method according to the invention.

In one example of the invention, the method further comprises applying a cover over the injured site of the cornea after the injection of the corneal stem cell-based implant according to the invention.

In the invention, the cover used for covering the injured site may include, but not limited to, a collagen layer or disc, a therapeutically contact lens, and a sheet or disc of amniotic membrane.

According to the examples of the invention, the stem cells that may be used in the invention includes but not limited to corneal epithelial stem cells, mucosal stem cells, induced pluripotent stem cells, mesenchymal stem cells, and a combination thereof.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated herein by reference in their entirety.

EXAMPLE

1. Materials and Methods 1.1 Chemicals

Carboxymethyl-hexanoyl Chitosan (CHC) was bought from Advance Delivery Technology Inc., Hsinchu, Taiwan. Glycerol was bought from Sigma-Aldrich. β-glycerol phosphate disodium salt hydrate was bought from Merck. Genipin was purchased from Callenge Bioproducts Co., Taiwan.

1.2 Preparation of CHC pre-nanogel solution

The amphiphic CHC powder as used herein was prepared as previously described in U.S. application Ser. No. 13/079,439, filed on Apr. 4, 2011. Pre-nanogel solution was prepared as follows: 0.5-3 g of CHC powder was dissolved in 100 ml distilled phosphate buffer solution (PBS) to prepare 0.5-3% (w/v) CHC solution, the solution was then cooled in an ice bath. Subsequently, glycerol was dropped into the CHC solution in ice bath to prepare a pre-nanogel solution containing 0.1-10% (w/v) glycerol.

1.3 Preparation of the nanogel for culturing stem cells in vitro

Stem cells were harvested from sub-confluent cultures by use of trypsin and re-suspended in 193.2 µl of PBS to give a cell suspension with a total cell number of $1.256 \times 10^6$. To prepare a 2.15% nanogel solution, the cell suspension was further mixed with 62.8 µl of β-glycerol phosphate disodium salt hydrate and followed by the addition of 1 ml of 2.7% pre-nanogel solution, all of which were conducted at 4° C. After a thorough stifling of the mixture for about 20 min, 500 µl of the resulted nanogel solution in which stems cells were now embedded was added to wells of a 24-well plate and then incubated at 37° C. for 30 min for a sol-to-gel transition. For stem cells cultured in the formed nanogel with medium, 1 ml of maintain medium was further added onto the top of the formed nanogel. A diagram illustrating the process for preparing the nanogel for culturing stem cells in vitro was shown in FIG. 1. The formed nanogel with or without medium was then subjected to the determination of cell viability by green fluorescent protein gene imaging or MTT assay and stemness gene expression by real-time PCR.

1.4 Determination of stem cell viability by green fluorescent protein gene (GFP) imaging and MTT assay For cell viability tests using GFP imaging, the GFP-positive stem cell numbers were measured under the fluorescent microscope (Olympic IX71), and the analysis of the fluorescent intensity was further performed by Image Pro-Plus software (Medium Media Cybernetics, USA). Cell proliferation rates can also be evaluated by MTT assay. Briefly, $2 \times 10^4$ stem cells were seeded in each well of a 24-well plate to allow the cells to attach. After incubation at 37° C. with air containing 5% CO2 for one day, the medium was replaced with 1 ml MTT solution (0.25 mg/ml of 3-(4,5-dimethylthiazol-2yl)-2,5-diphenyltetrazolium bromide) and incubation was continued for another 4 hours. 100% isopropanol was then added to terminate the reaction and the absorbance was monitored using a microplate reader (SpectraMax 250, Molecular Devices, Sunnyvale, Calif., USA.) at a wavelength of 560 nm.

1.5 Preparation of the injectable stem cell-based implant

Figure 2:
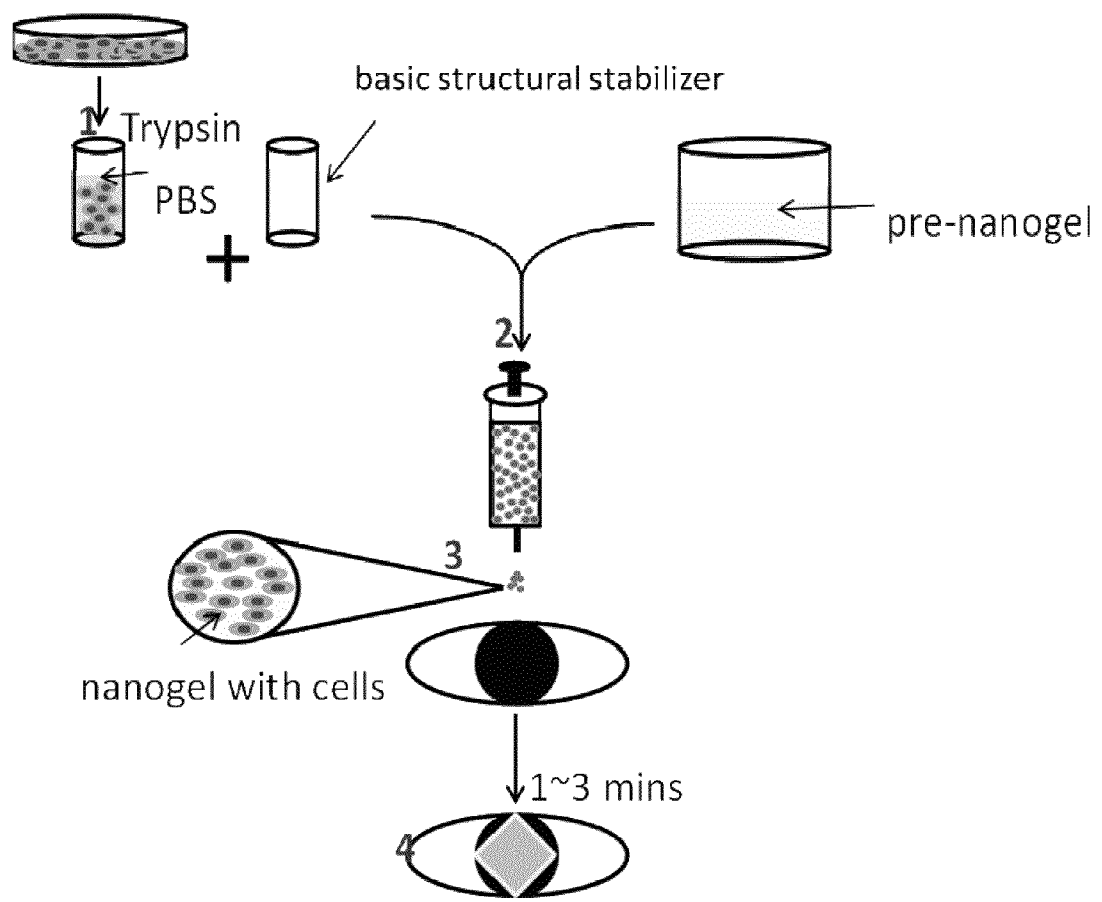
FIG. 2 is a flow chart showing the process for preparing the injectable stem cell-based implant.
Figure 3:
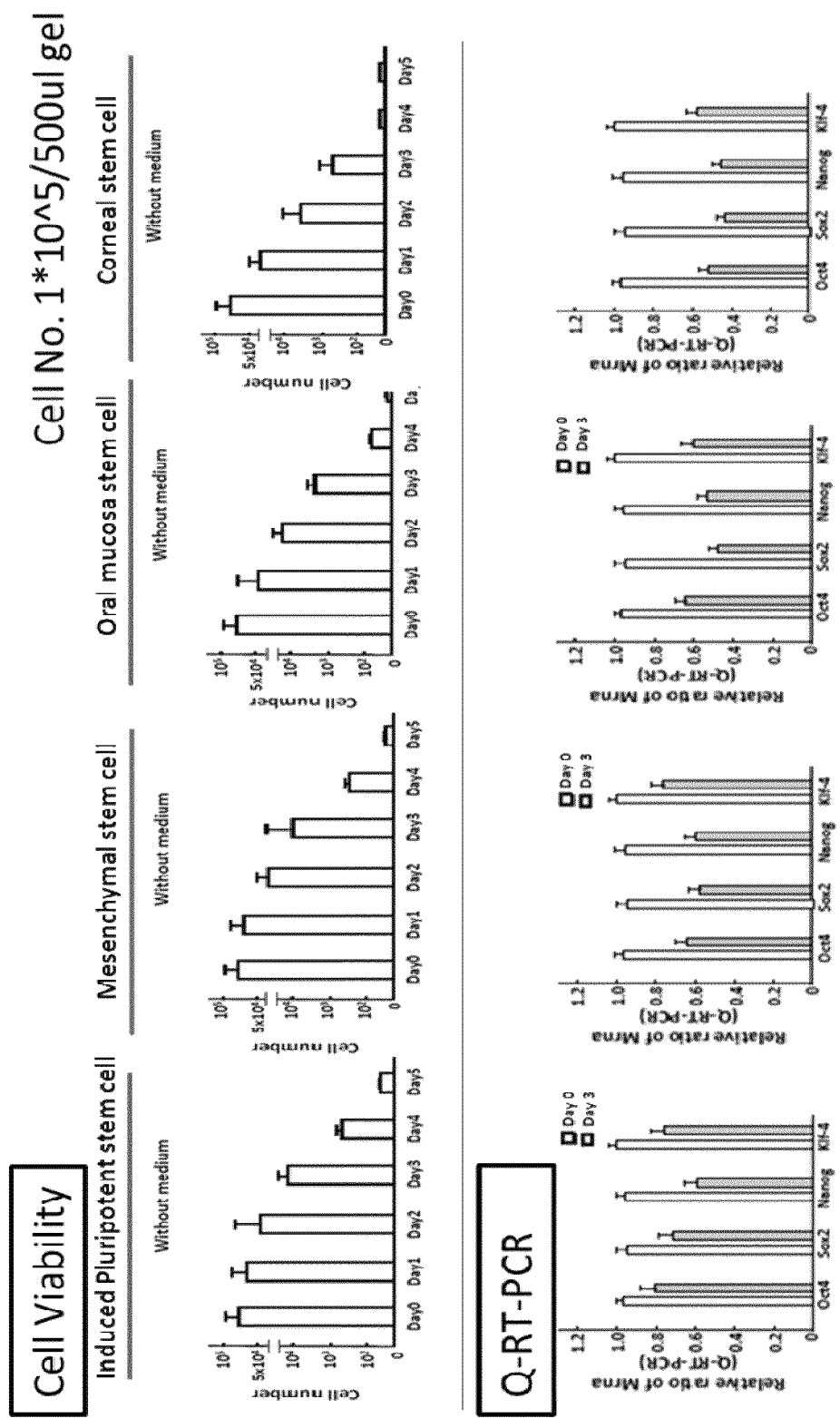
FIG. 3 provides a set of diagrams showing the proliferation rate measured by the fluorescent imaging analysis (upper line) and typical stemness properties detected by quantitative PCR (lower line) of the four types of stem cells cultured in nanogels without medium.
Figure 4:
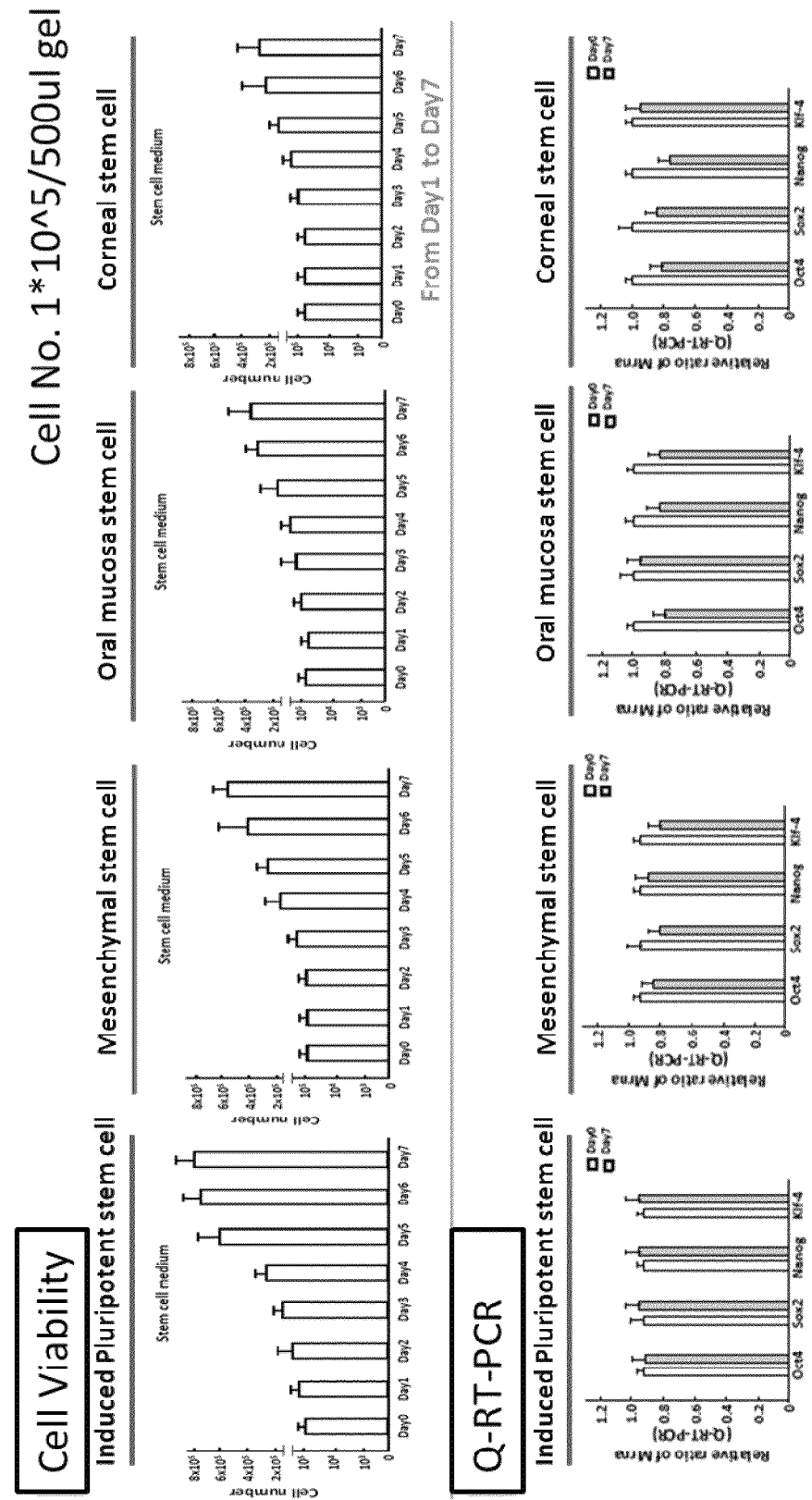
FIG. 4 provides is a set of diagrams showing the proliferation rate measured by the fluorescent imaging analysis (upper line) and typical stemness properties detected by quantitative PCR (lower line) of the four types of stem cells cultured in nanogels with medium.
Figure 5:
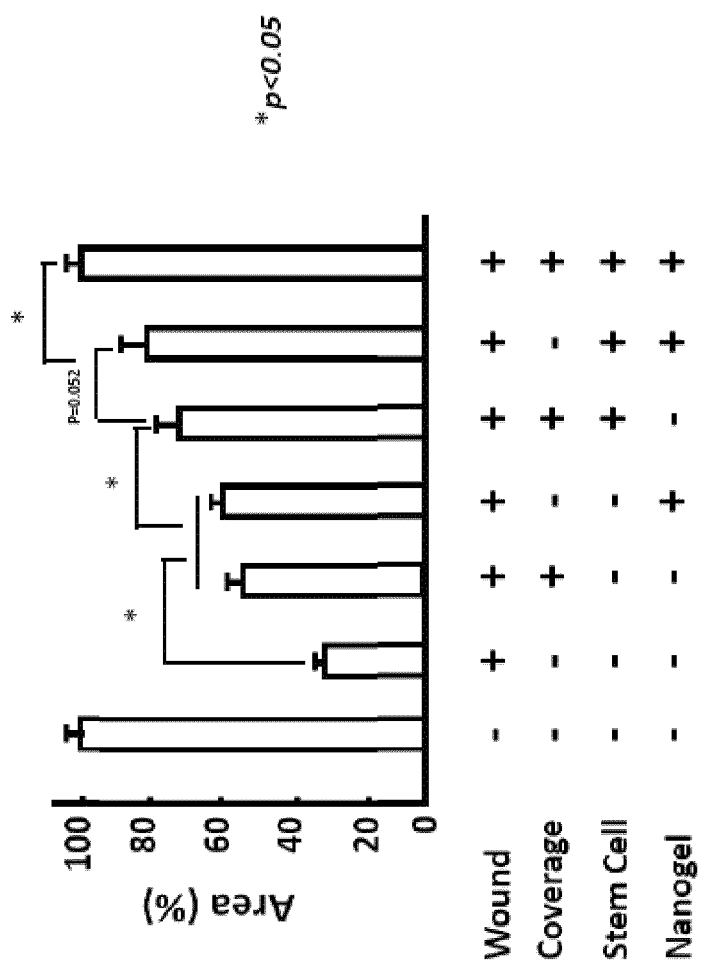
FIG. 5 provides a diagram showing the percentage of repaired areas analysed on Day 7 by Motic Images Advanced 3.0; wherein the data were calculated as "defect area of cornea/original wounded area×100%" and were expressed with mean+/− standard error (SEM); P values were calculated by t-test of Sigma Statistical Software; and $p<0.05$ is considered significant and marked with the symbol "*".

Corneal stem cells were harvested from sub-confluent cultures by use of trypsin and re-suspended in 115.3 µl of PBS to give a cell suspension with a total cell number of $1.174 \times 10^6$. To prepare a 2.3% nanogel solution, the cell suspension was further mixed with 58.7 µl of β-glycerol phosphate disodium salt hydrate and followed by the addition of 1 ml of 2.7% pre-nanogel solution, all of which were conducted at 4° C. After a thorough stifling of the mixture for about 20 min, 125 µl of the resulted nanogel solution containing stems cells was injected onto the damaged cornea of a tested rat. After a period of 1-3 min for gelation, the injected nanogel on the wound area can be further fixed by a cover such as a disc of amniotic membrane or a therapeutic contact lens. A diagram illustrating the process for preparing the injectable nanogel solution for stem cell transplantation is shown in FIG. 2.

2. Results 2.1 Evaluation of Stem Cell Viability and Cultivation in Nanogel

To assess the potential ability of nanogel to sustain the viability of stem cells, four types of stems cells were used in this study, including epithelial corrneal stem cells, oral mucosal stem cells, induced pluripotent stem cells (iPSCs), and mesenchymal stem cells. Before co-culture of these stem cells in nanogel with or without medium, the stem cells were transduced with green fluorescent protein gene (GFP) by lentiviral vector system. For capturing a higher percentage of GFP-positive cells, a sorting system of cell flow cytometry was used to isolate the GFP-positive cell from the lentiviral-GFP infected stem cells. After this, pure clones of these four types of GFP-positive stem cells were established for long-term co-culturing with pre-nanogel as described in Materials and Methods 1.3.

The nanogel of the present invention can be used to serve as a niche for cultivating all of the four types of stems cells. Moreover, a daily record of cell numbers which presented green fluorescent signals substantiates the fact that nanogel without any culture medium and supplements can be used to sustain stem cell viability for at least 3 days (as shown in the upper line of 3). In addition, in order to understand whether critical stemness signatures could be maintained by stem cells cultured in nanogel with medium, we further detected the mRNA expression levels of stemness genes, including Oct4, Sox2, Nanog, and Klf-4, in the four types of stems cells by quantitative RT-PCR method. As shown in the lower line of 3, expression levels of these genes were still detectable in samples taken from Day 3, further illustrating that nanogel alone can maintain the self-renewal ability and pluripotent property of stem cells.

It was found that stem cells could persistently proliferate for at least 7 days in nanogel with culture medium (as shown in the upper line of 4), and by detecting the four stemness genes using quantitative RT-PCR, it was further indicated that these cells perfectly maintained their stemness signatures for at least the same period, as shown in the lower line of 4.

Given the above, the data demonstrated that nanogel was able to provide a niche for stem cells to proliferate when supplemented with culture medium and more importantly, it was evidenced to serve as a carrier to sustain stem cell viability, either with or without culture medium.

2.2 Evaluation of Therapeutic Potential of Nanogel for Cell Transplantation in Corneal Damaged Model Eight (8) weeks old Sprague-Dawley rats weighing around 250 grams, were divided into seven groups: the "normal" group (without any injury or treatment), the "wound" group (with injured cornea but no treatment), the "coverage" group (with injured cornea to be covered with a piece of amniotic membrane), the "nanogel only" group (with injured cornea to be covered with nanogel only), the "Cov.+Stem cell" group (with injured cornea to be treated with corneal epithelial stems cells and further fixed with a piece of amniotic membrane), the "NG+Stem cell" group (with injured cornea to be treated with nanogel containing corneal epithelial stem cells), and the "Cov.+NG+Stem cell" group (with injured cornea to be treated by nanogel containing corneal epithelial stem cells and further fixed with a piece of amniotic membrane). The groups with injured cornea were established by abrasion with surgical blade plus 0.05% mitomycin C. After abrasion, all groups except for the "normal" group were then subjected to the different treatments as indicated above. The injectable nanogel with stem cells to be used for the treatment of injured cornea was prepared as descried in Materials and Methods 1.5. For evaluating the corneal healing rate of each group, we keep a daily healing record of the wounded area by staining the cornea of each group with fluorescence dye and detecting positive signals under UV light exposure. Analysis of the corneal healing ability was conducted by use of Motic Images Advanced 3.0 and the data were calculated as "defect area/original wounded area×100%." The percentages of repaired areas analysed are shown in 5.

Figure 6:
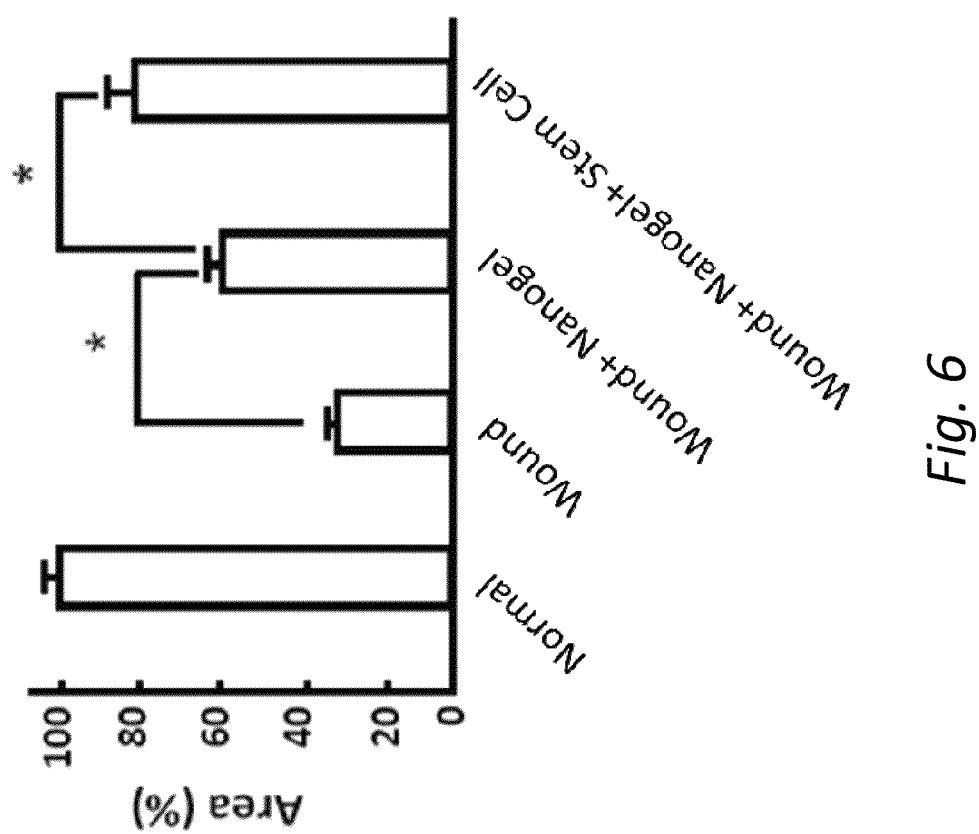
FIG. 6 is a diagram showing the efficacy of the nanogel in combination of stem cells to repair injured cornea.

It was demonstrated that on Day 7 after transplantation, damaged cornea treated with nanogel carried with corneal epithelial stem cells and further fixed with coverage presented the highest healing rate, as the repaired area was almost 100% compared to the "normal" group. More importantly, the group treated by use of nanogel carried with corneal epithelial stem cells without any coverage (the "NG+Stem cell" group) displayed a significantly higher healing rate compared to the "wound" group. Notably, the healing rate in the "NG+Stem cell" group was slightly better than that in the "Cov.+Stem cell" group. The effects of the nanogel in combination of stem cells without any coverage were more apparent in FIG. 6.

Figure 7:
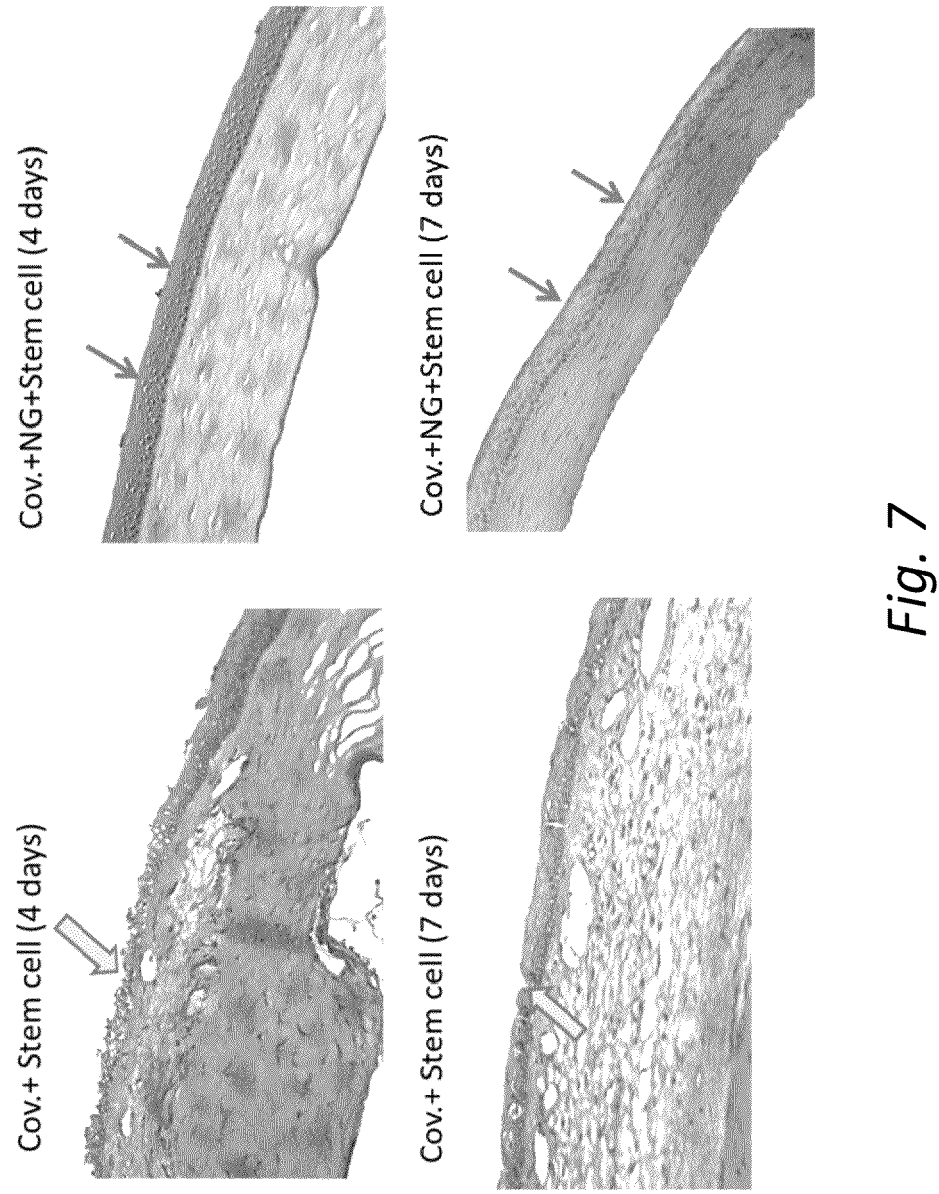
FIG. 7 is a set of images of immunohistochemical staining showing the effect of amphiphilic nanogel-based stem cell therapy as compared to the traditional ex vivo amniotic membrane-based therapy on the injured cornea of the tested rats.

In order to further assess the potential wound healing ability of the nanogel as compared to that of the conventional amniotic membrane-based stem cell therapy, the cornea samples of the "Cov.+NG+Stem cell" and the "Cov.+Stem cell" groups were checked by immunohistochemical staining. Consistently, histostaining data revealed that the nanogel containing corneal epithelial stem cells in combination with amniotic membrane reduced the lesions of the corneal section to a greater extent on both DAY 4 and Day 7 compared to the "Cov.+Stem cell" group. The representative images of the sections were shown in FIG. 7.

The results demonstrated that the nanogel could serve as a better and more efficient stem cell-based implant for stem cell therapy as compared to the traditional ex vivo amniotic membrane-based cell therapy.

We claim:

1. A method for repairing a tissue damage in a subject, comprising injecting an injectable stem cell-based implant to the site of the tissue damage of the subject, wherein the injectable stem cell-based implant is prepared by adding stem cells to a solution comprising an amphiphilically modified carboxymethyl-hexanoyl chitosan with glycerol as a solvent, and stabilizing the stem-cell containing solution in β-glycerol phosphate disodium hydrate to produce the injectable stem cell-based implant in the form of a solution, which gelates after the injection where the temperature rises to 30~40° C.;

wherein the amphiphilically modified carboxymethyl-hexanoyl chitosan is of formula (I)

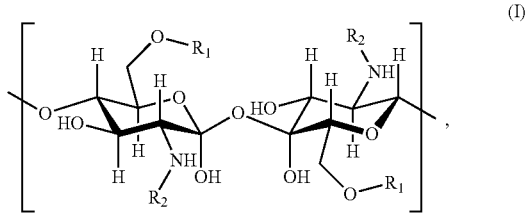

in which R1 is $CH_2COOH$ or H; and R2 is $CO(CH)_4CH_3$, $CH_2COOH$, or $COCH_3$ or H.

2. The method of claim 1, wherein the injectable stem cell-based implant is prepared at 4~20° C. by a method comprising the steps of:
   (a) stirring a solution comprising glycerol as a solvent and 0.1-10% (w/v) of the amphiphilically modified carboxymethyl-hexanoyl chitosan to obtain a pre-nanogel solution; and
   (b) adding the stem cells and 0.1-10% (w/v) of β-glycerol phosphate disodium hydrate to the pre-nanogel solution obtained in step (a) to produce a stem cell-containing solution, and
   (c) stirring the stem cell-containing solution obtained in step (b) thoroughly to obtain the injective stem cell-based implant.

3. The method of claim 2, wherein the stem cells are cultured at 37° C. for cell growth prior to step (b).

4. The method of claim 1, wherein the tissue damage occurs in cornea, and wherein the injectable stem cell-based implant, which contains corneal stem cells, is prepared by the method comprising the steps of:
   (a) stirring 0.1-10% (w/v) of the amphiphilically modified carboxymethyl-hexanoyl chitosan with glycerol as a solvent to obtain a pre-nanogel solution at 4~20° C.; and
   (b) adding the corneal stem cells and 0.1-10% (w/v) of β-glycerol phosphate disodium hydrate to the pre-nanogel solution obtained in step (a) to produce a stem cell-containing solution; and
   (c) stirring the stem cell-containing solution obtained in step (b) thoroughly at 4~20° C. to obtain the injectable stem cell-based implant that contains the corneal stem cells.

5. The method of claim 4, further comprising applying a cover over the injured site after the injection of the stem cell-based implant that contains the corneal stem cells.

6. The method of claim 5, wherein the cover is selected from the group consisting of a collagen layer or disc, a therapeutically contact lens and a sheet or disc of amniotic membrane.

7. The method of claim 1, wherein the tissue damage occurs in cornea and wherein the stem cell-based implant contains corneal stem cells.

* * * * *